United States Patent [19]
Hiraki et al.

[11] Patent Number: 5,900,363
[45] Date of Patent: * May 4, 1999

[54] **PROCESS FOR PRODUCING ε-POLY-L-LYSINE WITH IMMOBILIZED *STREPTOMYCES ALBULUS***

[75] Inventors: Jun Hiraki; Eriko Suzuki, both of Yokohama, Japan

[73] Assignee: Chisso Corporation, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/662,061

[22] Filed: Jun. 4, 1996

Related U.S. Application Data

[63] Continuation-in-part of application No. 08/435,844, May 5, 1995, abandoned, which is a continuation of application No. 08/196,767, Feb. 15, 1994, abandoned, which is a continuation of application No. 08/022,311, Feb. 25, 1993, abandoned.

[30] Foreign Application Priority Data

Feb. 26, 1992 [JP] Japan ........................... 4-75484

[51] Int. Cl.$^6$ .................................................. C12P 21/04
[52] U.S. Cl. ...................... 435/71.2; 435/252.35; 435/174
[58] Field of Search ...................... 435/106, 174, 435/71.2

[56] References Cited

U.S. PATENT DOCUMENTS

| | | | |
|---|---|---|---|
| 4,138,292 | 2/1979 | Chibata et al. | 435/176 |
| 4,276,381 | 6/1981 | Sakimae et al. | 435/179 |
| 5,294,552 | 3/1994 | Hiraki et al. | 435/252.3 |
| 5,434,060 | 7/1995 | Hiraki et al. | 435/71.2 |

OTHER PUBLICATIONS

Heinrich et al, European J. Appl. Microbiol. Biotechnol. 15:88–92 (1982).

Mattiasson, Immobilized Cells and Organelles, vol. 1, CRC Press, Inc. : Boca Raton, Florida, (1983), pp. 8–13.

Shima et al., Agric. Biol. Chem., 45(11):2497–2502, (1981).

Shima et al, Agric. Biol. Chem, 45(11):2497–2502, (1981).

Hartmeier, *Immobilized Catalysts*, Springer–Verlag: New York, 1988, p. 45.

*Primary Examiner*—Irene Marx
*Attorney, Agent, or Firm*—Leydig, Voit & Mayer, Ltd.

[57] ABSTRACT

An effective process for producing ε-poly-L-lysine is provided, which process comprises cultivating a microorganism having ε-poly-L-lysine productivity, such as a bacterium belonging to the Streptomyces genus, in the form of immobilized bacterial cells under aerobic conditions, and according to which process, the bacterial cells cause no bacteriolysis; the immobilized bacterial cells retaining ε-poly-L-lysine productivity can be easily separated and recovered from the culture solution containing ε-poly-L-lysine; and semi-continuous or continuous production of ε-poly-L-lysine by the use of the immobilized bacterial cells is possible.

14 Claims, No Drawings

PROCESS FOR PRODUCING ε-POLY-L-LYSINE WITH IMMOBILIZED *STREPTOMYCES ALBULUS*

This is a continuation-in-part of application Ser. No. 08/435,844, filed on May 5, 1995, which is a continuation of application Ser. No. 08/196,767, filed Feb. 15, 1994, which is a continuation of application Ser. No. 08/022,311, filed on Feb. 25, 1993 all now abandoned.

BACKGROUND OF THE INVENTION

1. Field of the Invention

This invention relates to a process for producing ε-poly-L-lysine using immobilized bacterial cells.

2. Description of the Related Art

ε-Poly-L-lysine has already been known to be obtained by cultivating *Streptomyces albulus* subsp. *lysinopolymerus* No. 346 (Japanese patent application laid-open No. Sho 53-72896), for example.

The above substance is a homopolymer of L-lysine, that is, a high molecular weight compound obtained by binding an amino group at the ε-position of L-lysine to a carboxyl group of an adjacent L-lysine by means of a peptide bond.

Since the above substance is a polymer of L-lysine, which is an essential amino acid, it is very safe, and, since it has a high cation content, it has specific physical properties. Thus, by making use of these properties, various use applications to e.g., toiletries, cosmetic preparations, feed additives, pesticides, food additives, and electronic materials, etc, have been developed.

A conventional process for producing ε-poly-L-lysine has been carried out as follows:

Bacterial cells belonging to the Streptomyces genus having ε-poly-L-lysine productivity are cultivated under aerobic conditions, followed by adjusting the pH to that in the vicinity of 4 after the growth of the bacterial cells have been confirmed, continuing the cultivation, separating the bacterial cells from the culture solution containing ε-poly-L-lysine by means of centrifugation or filtration, and purifying the bacterial cells by means of a basic anionic exchange resin treatment (Japanese patent application laid-open No. Hei 02-020295) or a cationic exchange resin treatment (Japanese patent application laid-open No. Hei 02-092927), for example.

However, according to such a conventional process of cultivating bacterial cells of the Streptomyces genus having ε-poly-L-lysine productivity under aerobic conditions and accumulating ε-poly-L-lysine in the culture solution, the viscosity of the culture solution becomes high and the bacterial cells cause bacteriolysis and hence, it is impossible to reuse the bacterial cells. Further, when centrifugal separation or filtration is carried out in order to separate the bacterial cells, a long time is required because the bacterial cells have caused bacteriolysis.

For example, to remove the bacterial cells from a culture solution of 10 $m^3$ using a filtration apparatus having a filtration area of 10 $m^2$, about 32 hours are required; hence, such a long time has caused a serious hindrance to production. Still further, since the bacterial cells cause bacteriolysis, recovery of only the culture solution is difficult; hence, it is difficult to carry out a semi-continuous cultivation, wherein, for example, a fresh medium is added. The above factors hinder reduction in the production cost of ε-poly-L-lysine.

Thus, if it is possible to inhibit higher viscosity of the culture solution due to bacterial cells and the bacteriolysis of bacterial cells, it is possible to reduce the production cost of ε-poly-L-lysine. The present inventors have extensively researched a process for achieving the above object. As a result, we have found that, when a microorganism capable of producing ε-poly-L-lysine is immobilized, the above-mentioned problems are solved at a single stroke, and have achieved the present invention.

As apparent from the foregoing, the object of the present invention is to provide a novel and efficient process for producing ε-poly-L-lysine, wherein, when ε-poly-L-lysine is produced using a microorganism, immobilized bacterial cells are used, whereby higher viscosity of the culture solution and bacteriolysis of the bacterial cells are inhibited, the recovery of the culture solution containing ε-poly-L-lysine and the purification of ε-poly-L-lysine from the recovered culture solution become easy, and the separated, immobilized bacterial cells are repeatedly used and semi-continuously or continuously used as the catalyst for producing ε-poly-L-lysine. In addition, the semicontinuous production referred to herein means a production wherein a medium containing a substrate or materials is added to a reactor containing the immobilized bacterial cells and the total quantity of this medium is exchanged with a fresh medium after a definite time, whereby ε-poly-L-lysine is repeatedly produced.

SUMMARY OF THE INVENTION

The present invention has the following aspects (1), (2), (3), (4) and (5):

(1) A process for producing ε-poly-L-lysine, which comprises cultivating a microorganism capable of producing ε-poly-L-lysine in the form of immobilized bacterial cells under aerobic conditions.

(2) A process for producing ε-poly-L-lysine according to item (1), which is carried out semicontinuously or continuously.

(3) A process for producing ε-poly-L-lysine according to item (1), wherein the microorganism having ε-poly-L-lysine productivity is a bacterium belonging to the Streptomyces genus.

(4) A process for producing ε-poly-L-lysine according to item (2), wherein the microorganism having ε-poly-L-lysine productivity is a bacterium belonging to the Streptomyces genus.

(5) A process for producing ε-poly-L-lysine according to item (1), wherein the microorganism having ε-poly-L-lysine productivity is immobilized according to a method selected from the group consisting of an adsorption method, a cross-linking method and an entrapping method.

(6) A process for producing ε-poly-L-lysine according to item (2), wherein the microorganism having ε-poly-L-lysine productivity is immobilized according to a method selected from the group consisting of an adsorption method, a cross-linking method and an inclusion method.

(7) A process for producing ε-poly-L-lysine according to item (1), wherein the microorganism having ε-poly-L-lysine productivity is immobilized according to a combination of an adsorption method with a cross-linking method or a combination of an adsorption method with an entrapping method.

(8) A process for producing ε-poly-L-lysine according to item (2), wherein the microorganism having ε-poly-L-lysine productivity is immobilized according to a combination of an adsorption method with a cross-linking method or a combination of an adsorption method with an entrapping method.

DETAILED DESCRIPTION OF PREFERRED EMBODIMENTS

The constitution and effectiveness of the present invention will be described in more detail.

As the microorganisms used in the present invention, any of microorganisms having ε-poly-L-lysine productivity or capable of producing ε-poly-L-lysine may be used.

As such microorganisms, for example, *Streptomyces albulus* subsp. *lysinopolymerus* No. 346 (Japanese patent application laid-open No. Sho 53-72896) variants thereof that produce ε-poly-L-lysine in a notably large quantity (Japanese patent application laid-open No. Sho 63-49075; deposited Jul. 22, 1986 as No. 11011A-1 (Deposit No. 1110, Ferm BP-No. 1109) at Fermentation Research Institute of the Agency of Industry, Science, and Technology (Japan), located at 1-3, Higashi 1-chome, Yatabe-machi Tsukuba-gu, Ibaraki-Ken, 305, Japan) and *Streptomyces noursei* (Japanese patent application laid-open No. Hei 1-187090), etc., are known. A preferred strain of *Streptomyces albulus* subsp. *lysinopolymerus* is No. 11011A-1.

Further, the immobilization of the producing bacterium used in the present invention can be carried out according to a general method or application of a general method. For example, an adsorption method, a crosslinking method, an entrapping method, or a covalent bond method, etc., may be used.

The immobilized bacterial cells may be prepared according to a single immobilization method. Further, an immobilization method also can be carried out in using a combination of two of the above methods. Among the above methods, the adsorption method and the entrapping method are preferably employed, since according to the methods, the immobilization is easy and a stabilized activity is obtained and further, when the activity is reduced, reactivation can be carried out. The entrapping method,is generally carried out by entrapping the bacterial cells in a high molecular weight polymer gel, such as polyacrylamide gel, polyurethane gel, photo-crosslinkable resin, etc. In the present invention, however, since the ε-poly-L-lysine to be produced is a basic substance, it is preferred not to use an acidic, high molecular weight compound gel, which adsorbs the substance, such as carrageenan gel, alginic acid gel, etc.

As the adsorption method, a method of immobilization onto a porous substance or a non-woven cloth is particularly preferred. As the porous substance, for example, porous ceramics, porous glass, cellulose: sponge, sintered metal porous body, and materials prepared from polyvinyl chloride, polyethylene, polypropylene, polystyrene, and polyurethane, etc. also may be used.

As the above method of entrapping in a polyacrylamide gel, for example, acrylamide monomer, N,N'-methylenebisacrylamide as a crosslinking agent and a live bacterial cells are suspended in a buffer, ammonium persulfate as a polymerization initiator and β-dimethylaminopropionitrile as a polymerization promoter are added to the buffer, and the mixture is subjected to a polymerization reaction at room temperature for about 30 minutes to obtain immobilized bacterial cells.

Further, in general, when thermoplastic resins are heated at a temperature of 150° to 250° C. for 0.5 to 5 hours, sintered bodies are obtained, and, when a suitable mold is used at the time of the heating, sintered porous bodies having various shapes are obtained. Still further, as to voids, pore size, strength, etc., when the conditions of sintering temperature, sintering time, packing of resin, thickening agent, quantity of water added, etc., are varied, preferred porous bodies are obtained. In addition to the above porous substances, any general commercially available products and processed products may be used as far as they can adsorb the present producing bacteria.

The porous substances are immersed in a buffer containing live bacterial cells to adsorb the microorganism, or the porous substance is contacted with a microorganism, since the initiation time of the cultivation and adhesion is affected along with the advance of the cultivation, whereby immobilized bacterial cells according to the process of the present invention are obtained.

The immobilized bacterial cells having ε-poly-L-lysine activity or productivity obtained according to the above process are cultivated in a usual ε-poly-L-lysine-producing medium or a medium having added glucose and ammonium sulfate or L-lysine in a buffer adjusted to an adequate pH, under aerobic conditions, to obtain a culture solution containing ε-poly-L-lysine. The immobilized bacterial cells are removed from the culture solution and ε-poly-L-lysine is purified with an ion exchange resin.

Further, the pH at the time of cultivation may fall within a range in which the microorganism having ε-poly-L-lysine productivity can produce ε-poly-L-lysine. A preferred pH is 4 to 7.

(Effectiveness of the Invention)

According to the process of the present invention, substantially no bacteriolysis of the bacterial cells during the cultivation occurs, the immobilized bacterial cells are easily removed, and an ε-poly-L-lysine solution containing no bacterial cells can be recovered in a short time, whereby an efficient production of poly-L-lysine becomes possible. Further, since it is easy to separate the immobilized bacterial cells from the culture solution, the culture solution is recovered after production of ε-poly-L-lysine, and a fresh medium is added to the immobilized bacterial cells, whereby a semi-continuous production of ε-poly-L-lysine can be carried out, or a fresh medium is added, while continuously discharging the culture solution, whereby a continuous production of ε-poly-L-lysine can be carried out. Thus, the present invention is very useful in that ε-poly-L-lysine can be produced effectively and commercially, at a low cost and over a long time, and can be fed to the fields of food additives, pesticides, and pharmaceuticals, etc. In all the examples, strain *Streptomyces albulus* subsp. *lysinopolymerus* No. 11011A-1 (Deposition No. 1110, Ferm BP-No. 1109) was used as a source of the immobilized bacterial cells.

EXAMPLE

The present invention will be described by way of Examples, but it should not be construed to be limited thereto.

Example 1

Into a 500 ml capacity shaking flask were placed a medium (pH 6.8, 50 ml) consisting of glucose (50 g/l), ammonium sulfate (10 g/l), yeast extract (5 g/l) potassium dihydrogenphosphate (1.36 g/l), sodium monohydrogenphosphate (1.58 g/l), magnesium sulfate (0.5 g/l), zinc sulfate (0.04 g/l) and ferrosulfate (0.03 g/l), followed by sterilizing the medium in a conventional manner, planting *Streptomyces albulus*, cultivating it under shaking at 30° C.

for 36 hours to obtain a pre-culture solution, subjecting it, after the cultivation, to centrifugal separation to collect the bacterial cells, twice washing the bacterial cells (wet weight of bacterial cells: 4.2 g) with sterilized water and using the resulting cells for immobilization.

Preparation of immobilized bacterial cells was carried out as follows:

Acrylamide (1.68 g), N,N'-methylenebisacrylamide (0.09 g), lysine hydrochloride (0.67 g) and the bacterial cells obtained according to the above method were suspended in tris-hydrochloric acid buffer (pH: 7.2, 4.8 ml) (tris: 2-amino-2-hydroxymethyl-1,3-propanediol), followed by adding to the mixed solution a 5% aqueous solution of β-dimethylaminopropionitrile (1.1 ml) and a 1% aqueous solution of potassium persulfate (1.1 ml), allowing the mixture to stand still under $N_2$-saturated condition at room temperature for 30 minutes to effect gelation, shaping the gel into a 5 mm cube, and sufficiently washing the resulting gel with Tris-hydrochloric acid buffer to obtain bacterial cells immobilized in polyacrylamide gel (11.2 g).

The resulting bacterial cells immobilized in the polyacrylamide gel were added to a medium (pH 4, 40 ml) consisting of glucose (50 g/l), L-lysine (10 g/l) and citric acid (20 g/l), followed by cultivation under shaking at 30° C. After 2 days, the content of ε-poly-L-lysine in the culture solution was determined to give 0.23 mg/ml.

Example 2

Bacterial cells immobilized in polyacrylamide gel (75 g), which were prepared in the same manner as in Example 1, were added to a conventional medium for cultivating ε-poly-L-lysine-producing bacterium (pH 4.2, 50 ml) consisting of glucose (50 g/l), ammonium sulfate (10 g/l), yeast extract (5 g/l), potassium dihydrogenphosphate (1.36 g/l), disodium monohydrogenphosphate (1.58 g/l), magnesium sulfate (0.5 g/l), zinc sulfate (0.04 g/l) and ferrosulfate (0.03 g/l), followed by cultivation under shaking at 30° C. After 2 days, the content of ε-poly-L-lysine in the culture solution was 0.20 mg/ml.

Example 3

Bacterial cells immobilized in polyacrylamide gel (100 g), which were prepared in the same manner as in Example 1, were added to a medium (pH 4, 1 l) consisting of glucose (50 g/l), L-lysine (10 g/l) and citric acid (20 g/l), followed by through-flow stirring cultivation at 30° C. by means of a 1.5 t capacity minijar fermenter, while adjusting the pH to 4. The content of ε-poly-L-lysine in the culture solution after cultivation for 48 hours was 1.5 g/l.

Thereafter, cultivation was continued, while successively adding glucose and L-lysine. The content of 6-poly-L-lysine after 125 hours was 10 g/l. The culture solution was subjected to centrifugal separation (3,000 G, 20 minutes) to remove the bacterial cells, followed by measuring the absorbance of the supernatant after the centrifugal separation at 660 nm. The absorbance was 0.008 less than the suitable absorbance of 0.010 or below or the preferred absorbance of 0.009 or below, and the bacterial cells were completely removed.

Comparative Example 1

Into a 500 ml capacity shaking flask were placed a medium (pH 6.8, 50 ml) consisting of glucose (50 g/l), ammonium sulfate (10 g/l), yeast extract (5 g/l), potassium dihydrogenphosphate (1.36 g/l), sodium monohydrogenphosphate (1.58 g/l), magnesium sulfate (0.5 g/l), zinc sulfate (0.04 g/l) and ferrosulfate (0.03 g/l), followed by sterilizing the mixture in a conventional manner, inoculating *Streptomyces albulus*, and cultivating under shaking at 30° C. for 36 hours to prepare a pre-culture solution.

This pre-culture solution was planted in a 1.5 l capacity minijar fermenter containing the same medium as the above (1 l), followed by through-flow stirring cultivation at 30° C. After the cultivation, when the pH of the culture solution dropped to about 4.2, glucose was successively added so as to give a concentration of 50 g/l, while adjusting its pH to 4.2 with aqueous NaOH solution, and continuing the cultivation.

The content of ε-poly-L-lysine in the culture solution after 125 hours was 12 g/l. This culture solution was subjected to centrifugal separation (3,000 G, 20 minutes) to remove the bacterial cells and the absorbance of the supernatant at 660 nm was measured. The absorbance was 0.282, so that the removal of the bacterial cells was insufficient.

From the above results, it was confirmed to be able to easily remove the bacterial cells by using the immobilized bacterial cells of the present invention.

Example 4

Bacterial cells (wet weight: 2.0 g), which were cultivated and recovered in the same manner as in Example 1, were suspended in a 0.1M phosphoric acid buffer (2 ml), followed by adding and mixing an a urethane prepolymer (3 g, M.W.: about 3,000) having a structure shown in formula 1, while stirring and effecting gelation, to obtain immobilized bacterial cells of polyurethane gel shaped into a 5 mm cube.

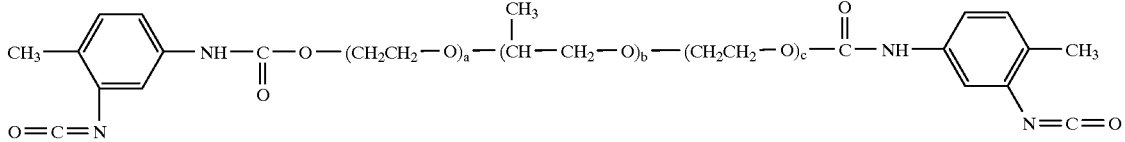

The bacterial cells immobilized in the polyurethane gel were added to a medium (pH 4, 40 ml) containing glucose (50 g/l), 1-lysine (10 g/l) and citric acid (20 g/l), followed by cultivating the mixture under shaking at 30° C. and measuring the quantity of ε-poly-L-lysine in the culture solution after 2 days and 3 days. The quantities of ε-poly-L-lysine in the culture solution were 0.31 g/l after 2 days and 0.47 g/l after 3 days.

Example 5

Cultivation under the same conditions as in Example 4 was carried out for 3 days, followed by removing the supernatant obtained by centrifugal separation (3,000 G, 20 minutes), adding a fresh medium (pH: 4, 40 ml) consisting of glucose (50 g/l), L-lysine (10 g/l) and citric acid (20 g/l) and cultivating the mixture under shaking at 30° C. After a lapse of 2 days after having added the fresh medium, the quantity of ε-poly-L-lysine in the culture solution was 0.75 mg/ml.

From the above results, it was confirmed that the immobilized bacterial cells of the present invention could be applied to a semi-continuous cultivation.

Example 6

Bacterial cells (wet weight: 2.0 g), which were cultivated and recovered in the same manner as in Example 1, were suspended in sterilized water (5 ml), and mixing a 15% aqueous solution (40 ml) of a photo-crosslinkable resin, ENT-2000 (tradename of product made by Kansai Paint Co., Ltd.), sterilized in an autoclave and a polymerization initiator (0.008 g) was added to the suspension, and the suspension was mixed, and irradated with ultraviolet rays (365 nm) while stirring for 30 minutes, to prepare a gel having immobilized bacterial cells. This gel was shaped into a 5 mm cube to obtain fixed bacterial cells (53 g).
The immobilized bacterial cells in the photo-crosslinkable resin were added to a medium (pH: 4, 100 ml) containing glucose (50 g/l), 2-lysine (10 g/l) and citric acid (20 g/l). The cells were then cultivated while shaking at 30° C. and the quantities of ε-poly-L-lysine in the culture solution after 2 days and 3 days were measured to give 0.44 g/l after 2 days and 0.57 g/l after 3 days.

Example 7

The bacterial cells precultivated in the same manner as in Example 1 were recovered by means of centrifugal separation and washed with sterilized water (wet bacterial cells weight: 4.0 g). Into a medium (pH: 6.8, 30 ml) consisting of glucose (50 g/l), ammonium sulfate (10 g/l), yeast extract (5 g/l), potassium dihydrogenphosphate (1.36 g/l), disodium monohydrogenphosphate (1.58 g/l), magnesium sulfate (0.5 g/l), zinc sulfate (0.04 g/l) and ferrosulfate (0.03 g/l), were placed the above bacterial cells and polyurethane sintered porous beads (size : φ5 mm, 2 g), followed by cultivation with slow shaking at 30° C.

After 30 hours, bacterial cells immobilized in a polyurethane sintered porous body were recovered. The immobilized bacterial cells were suspended in a medium (pH: 4, 50 ml) containing glucose (50 g/l), L-lysine (10 g/l) and citric acid (20 g/l), followed by cultivation under shaking at 30° C. The quantity of ε-poly-L-lysine in the culture solution after 2 days of the cultivation was 0.62 mg/ml.

Further, the culture solution was subjected to centrifugal separation (3,000 G, 20 minutes) and the absorbance of the resulting supernatant was measured at 660 nm. The absorbance was 0.009 and the bacterial cells were completely removed.

Example 8

Into a 400 ml capacity air bubble-through type reactor were fed a medium (pH 6.8, 100 ml) consisting of glucose (50 g/l), ammonium sulfate (10 g/l), yeast extract (5 g/l), potassium dihydrogen phosphate (1.36 g/l), disodium monohydrogen phosphate (1.58 g/l), magnesium sulfate (0.5 g/l), zinc sulfate (0.04 g/l) and ferrosulfate (0.03 g/l), and a porous block-form ceramic (made by Nihon Gaishi Co., Ltd.) (30 g), followed by sterilizing them in a conventional manner, incubating *Streptomyces albulus* taken from a slant medium for preserving bacterial cells in a quantity of one platinum loop, and carrying out aeration cultivation in an aeration quantity of 0.5 l/min. at 30° C. for 50 hours. The quantity of ε-poly-L-lysine in the culture solution after 50 hours was 0.3 g/l. Thereafter, only the culture solution was recovered, followed by adding to the immobilized bacterial cells in the reactor, a fresh medium (pH 4, 100 ml) consisting of glucose (50 g/l), L-lysine hydrochloride (10 g/l), citric acid (20 g/l), potassium dihydrogen sulfate (1.36 g/l), sodium monohydrogen phosphate (1.58 g/l), magnesium sulfate (0.5 g/l), zinc sulfate (0.04 g/l) and ferrosulfate (0.03 g/l), and carrying out aeration cultivation at 30° C. for 48 hours. The quantity of ε-poly-L-lysine in the culture solution after 48 hours was 3.7 g/l. Further, the culture solution was recovered, followed by adding a fresh medium and three times repeating a procedure of carrying out aeration cultivation at 30° C. for 48 hours. As a result, the quantities of ε-poly-L-lysine at the respective repeated times were as follows:

4.5 g/l (first time), 4.0 g/l (second time) and 5.2 g/l (third time).

From the foregoing, it was confirmed that, when medium exchange was repeated using the immobilized bacterial cells of the present invention, the semi-continuous production of ε-poly-L-lysine was effected.

Example 9

In a 400 ml capacity air bubble-through type reactor were placed a medium (pH 6.8, 100 ml) consisting of glucose (50 g/l), ammonium sulfate (10 g/l), yeast extract (5 g/l), potassium dihydrogen phosphate (1.36 g/l), disodium monohydrogen phosphate (1.58 g/l), magnesium sulfate (0.5 g/l), zinc sulfate (0.04 g/l) and ferrosulfate (0.03 g/l), and a porous cellulose sponge (Microcube FN-S03 (trademark of product made by Sakai Engineering Co., Ltd.)), followed by sterilizing the medium in a conventional manner, inoculating *Streptomyces albulus* taken from a slant medium for preserving bacterial cells in a quantity of one platinum loop, and carrying out aeration cultivation at 30° C. for 50 hours in an aeration quantity of 0.5 l/min. The quantity of ε-poly-L-lysine in the culture solution after 50 hours was 0.33 g/l. Thereafter, only the culture solution was recovered, followed by adding to the fixed bacterial cells in the reactor, a fresh medium (pH 4, 100 ml) consisting of glucose (50 g/l), L-lysine hydrochloride (10 g/l), citric acid (20 g/l), potassium dihydrogen phosphate (1.36 g/l), sodium monohydrogen phosphate (1.58 g/l), magnesium sulfate (0.5 g/l), zinc sulfate (0.04 g/l) and ferrosulfate (0.03 g/l), and carrying out aeration at 30° C. for 48 hours. The quantity of ε-poly-L-lysine in the culture solution after 48 hours was 2.9 g/l. Further, the culture solution was recovered, followed by adding a fresh medium and three times repeating a procedure of carrying out aeration cultivation at 30° C. for 48 hours. As a result, the quantities of ε-poly-L-lysine produced at the respective repetition times were as follows:

3.0 g/l (first time), 2.5 g/l (second time) and 2.0 g/l (third time).

From the foregoing, it was confirmed that, when the medium exchange was repeatedly carried out using the immobilized bacterial cells of the present invention, a semi-continuous production of ε-poly-L-lysine was possible.

Comparative Example 2

Bacterial cells were cultivated without feeding the ceramic carrier in Example 8. Namely, in a 400 ml capacity air bubble-through type reactor was placed a medium (pH 6.8, 100 ml) consisting of glucose (50 g/l), ammonium sulfate (10 g/l), yeast extract (5 g/l), potassium dihydrogen phosphate (1.36 g/l), disodium monohydrogen phosphate (1.58 g/l), magnesium sulfate (0.5 g/l), zinc sulfate (0.04 g/l) and ferrosulfate (0.03 g/l), followed by sterilizing the medium in a conventional manner, inoculating *Streptomyces albulus* taken from a slant medium for preserving bacterial cells in a quantity of one platinum loop and carrying out aeration cultivation at 30° C., in an aeration quantity of 0.5 l/min. for 50 hours. The quantity of $\epsilon$-poly-L-lysine in the culture solution after 50 hours was 0.25 g/l. Thereafter, bacterial cells were recovered from the culture solution by centrifuge (6,000 G, 15 min.), followed by adding to the recovered bacterial cells a fresh medium (pH 4, 100 ml) consisting of glucose (50 g/l), L-lysine hydrochloride (10 g/l), citric acid (20 g/l), potassium dihydrogen phosphate (1.36 g/l), sodium monohydrogen phosphate (1.58 g/l), magnesium sulfate (0.5 g/l), zinc sulfate (0.04 g/l) and ferrosulfate (0.03 g/l), and carrying out aeration at 30° C., for 48 hours. The quantity of $\epsilon$-poly-L-lysine in the culture solution after 48 hours was 1.3 g/l. Further, bacterial cells were recovered from the culture solution by centrifuge (6,000 G, 15 min.), followed by again adding the above fresh medium and carrying out aeration cultivation at 30° C. for 48 hours. The quantity of $\epsilon$-poly-L-lysine in the culture solution after 48 hours was 0.7 g/l.

From the above results, it was confirmed that, according to semi-continuous production of $\epsilon$-poly-L-lysine, wherein bacterial cells were recovered without using immobilized bacterial cells and cultivation was carried out, the productivity of $\epsilon$-poly-L-lysine became lower each cycle; hence semi-continuous production was difficult.

Example 10

In a 400 ml capacity air bubble-through type reactor were placed a medium (pH 6.8, 100 ml) consisting of glucose (50 g/l), ammonium sulfate (10 g/l), yeast extract (5 g/l), potassium dihydrogen phosphate (1.36 g/l), disodium monohydrogen phosphate (1.58 g/l), magnesium sulfate (0.5 g/l), zinc sulfate (0.04 g/l) and ferrosulfate (0.03 g/l), and a block-form ceramic (made by Nihon Gaishi Co., Ltd.) (30 g), followed by sterilizing them in a conventional manner, inoculating *Streptomyces albulus* taken from a slant medium in a quantity of one platinum loop and carrying out aeration cultivation at 30° C., in an aeration quantity of 0.5 l/min. for 50 hours. The quantity of $\epsilon$-poly-L-lysine in the culture solution after 50 hours was 0.3 g/l. Thereafter, a continuous production of $\epsilon$-poly-L-lysine over 300 hours was carried out, wherein addition into the reactor of a fresh medium (pH 4) consisting of glucose (50 g/l), L-lysine hydrochloride (10 g/l), citric acid (20 g/l), potassium dihydrogen phosphate (1.36 g/l), sodium monohydrogen phosphate (1.58 g/l), magnesium sulfate (0.5 g/l), zinc sulfate (0.04 g/l) and ferrosulfate (0.03 g/l) and withdrawal of the culture solution from the reactor were carried out at a rate of 2 ml/hr. The total quantity of $\epsilon$-poly-L-lysine produced over 300 hours was 2.2 g.

From the foregoing, it was confirmed that, when the medium exchange is continuously carried out using the immobilized bacterial cells, it is possible to easily carry out a continuous production of $\epsilon$-poly-L-lysine.

What we claim is:

1. A process for producing $\epsilon$-poly-L-lysine which consists essentially of cultivating *Streptomyces albulus* subsp. *lysinopolymerus* No. 11011A-1, Ferm BP-No. 1109, under aerobic conditions, at a pH of from about 4 to about 7, and at a temperature of 30° C. for 36–72 hours with shaking or aeration, wherein said Streptomyces are immobilized in a porous carrier or a non-acidic high molecular weight gel, and recovering $\epsilon$-poly-L-lysine.

2. The process for producing $\epsilon$-poly-L-lysine according to claim 1 in which the process is carried out semicontinuously.

3. The process for producing $\epsilon$-poly-L-lysine according to claim 1 in which the process is carried out continuously.

4. The process for producing $\epsilon$-poly-L-lysine according to claim 1, wherein said Streptomyces are immobilized by a method combining adsorption with cross-linking.

5. The process for producing $\epsilon$-poly-L-lysine according to claim 1, wherein said Streptomyces are immobilized by a method combining adsorption with entrapping.

6. The process for producing $\epsilon$-poly-L-lysine according to claim 1, wherein said Streptomyces are immobilized by adsorption.

7. The process for producing $\epsilon$-poly-L-lysine according to claim 1, wherein said Streptomyces are immobilized by cross-linking.

8. The process for producing $\epsilon$-poly-L-lysine according to claim 1, wherein said Streptomyces are immobilized by entrapping.

9. The process for producing $\epsilon$-poly-L-lysine according to claim 1, wherein said Streptomyces are immobilized by two or more of adsorption, cross-linking, and entrapping.

10. The process for producing $\epsilon$-poly-L-lysine according to claim 1, wherein substantially no bacteriolysis of said immobilized Streptomyces occurs.

11. The process for producing $\epsilon$-poly-L-lysine according to claim 1, wherein said immobilized Streptomyces are separated from the culture medium in which said Streptomyces are cultured and said culture medium has a measured absorbance at 660 nm of about 0.009 or less after separation from said Streptomyces.

12. A process for producing $\epsilon$-poly-L-lysine which consists essentially of cultivating *Streptomyces albulus* subsp. *lysinopolymerus* No. 11011A-1, Ferm BP-No. 1109, under aerobic conditions, at a pH of from about 4 to about 7, and at a temperature of 30° C. for 36–72 hours with shaking or aeration, wherein said Streptomyces are immobilized in a porous carrier comprising a non-acidic high molecular weight gel by a method combining adsorption with cross-linking or adsorption with entrapping and recovering $\epsilon$-poly-L-lysine.

13. The process for producing $\epsilon$-poly-L-lysine according to claim 12, wherein substantially no bacteriolysis of said immobilized Streptomyces occurs.

14. The process for producing $\epsilon$-poly-L-lysine according to claim 12, wherein said immobilized Streptomyces are separated from the culture medium in which said Streptomyces are cultured, wherein said culture medium has a measured absorbance at 660 nm of about 0.009 or less after separation from said Streptomyces.

\* \* \* \* \*